US00PP36081P2

(12) United States Plant Patent
Putnam

(10) Patent No.: US PP36,081 P2
(45) Date of Patent: Aug. 27, 2024

(54) GRAPE PLANT NAMED 'Harbinger'

(50) Latin Name: ***Vitis vinifera* x *Vitis riparia* x *Vitis rupestris***
Varietal Denomination: Harbinger

(71) Applicant: Alan R. Putnam, Hamilton, MT (US)

(72) Inventor: Alan R. Putnam, Hamilton, MT (US)

(73) Assignee: Alan R. Putnam, Hamilton, MT (US)

( * ) Notice: Subject to any disclaimer, the term of this patent is extended or adjusted under 35 U.S.C. 154(b) by 0 days.

(21) Appl. No.: 18/445,246

(22) Filed: Jun. 15, 2023

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206
See application file for complete search history.

(56) References Cited

U.S. PATENT DOCUMENTS

PP33,039 P2 * 5/2021 Walker ..... A01H 6/88
Plt./205

* cited by examiner

*Primary Examiner* — Susan McCormick Ewoldt

(57) ABSTRACT

A novel cultivar of grape plant named 'Harbinger' was discovered as a seedling in 2017. It was asexually propagated by rooting cuttings (the progeny) which in turn, have been scientifically evaluated for seven years. The characteristic of 'Harbinger' is its physiology, which enables complete ripening 3-4 weeks ahead of other red cold-hardy wine grapes (its Market Class). 'Harbinger' plants are winter-hardy to at least −20F, and present a good sugar/acid balance enabling quality red wine. Its most unique botanical characteristic is intense red-pigmentation in stems and petioles.

6 Drawing Sheets

Figure 1:
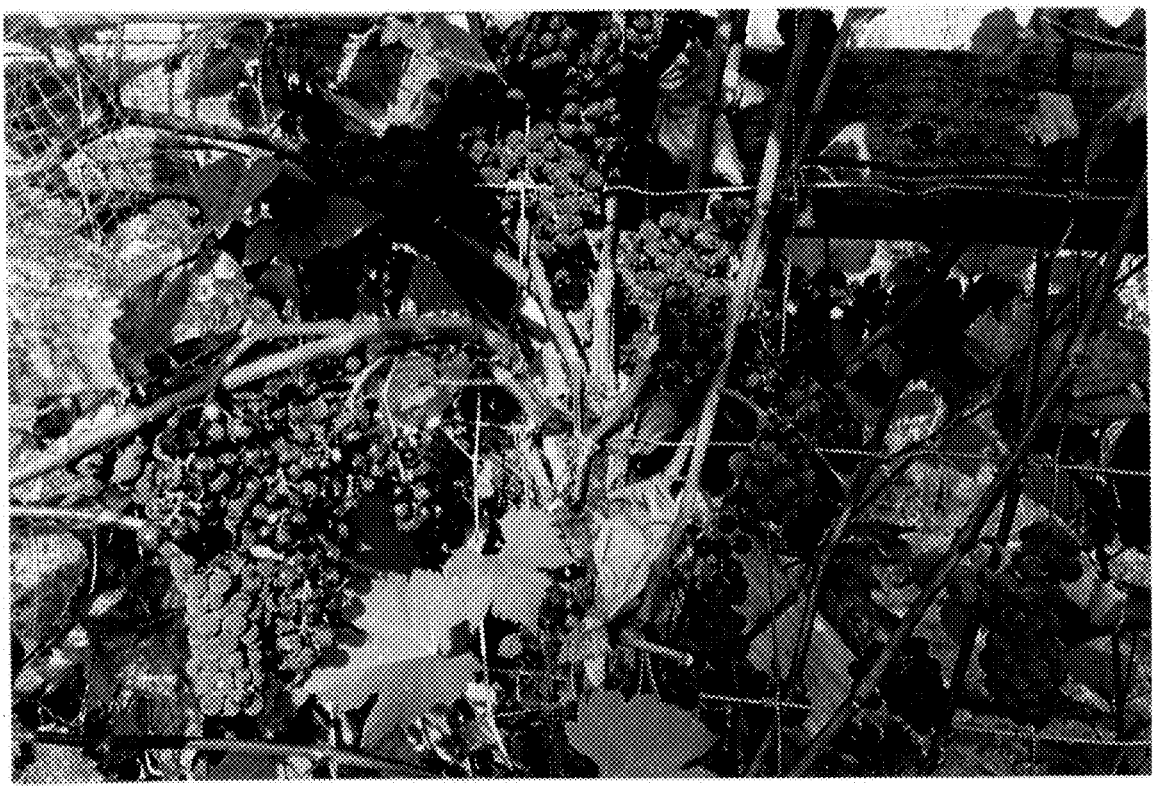

Botanical classification: *Vitis vinifera* x *Vitis riparia* x *Vitis rupestris.*
Variety denomination: 'HARBINGER'.

BACKGROUND OF THE INVENTION

Field of the Invention

'Harbinger' is a cold-hardy, red-wine grape, which resulted from an unknown genetic cross among 16 possible parents in an adjoining vineyard. The possible parents were *Vitis vinifera* x *Vitis riparia* or *Vitis rupestris* hybrids. The 'Harbinger' seed was vectored to a bordering fence row by a bird. This new cultivar will allow earlier production of red wines in cool-season regions, where existing cultivars often fall to completely ripen before frost. Clearly, 'Harbinger's Market Class is a cold -hardy, red-wine grape. There is commercial interest for a grape with these credentials from New England all the way to the Pacific Northwest.

Description of the Related Art

Most of the existing grape cultivars have been developed by intensive breeding efforts, where parents are selected and crossed. More rarely, crosses occur in nature that result in a desirable plant. The unique 'Harbinger' seedling was one of about 50 that occurred along the fence surrounding the vineyard at 822 Promise Lane, Corvallis, Montana. The seedling was identified as distinct in 2017 because of its early ripening, and assigned a code number, PUT101. Later, the original seedling (mother plant), and its progeny (rooted cuttings) were named 'Harbinger'.

Asexual propagation was achieved by the traditional method for grapes. Dormant cuttings were taken from the original 'Harbinger' seedling in March of 2018. The cuttings averaged 15 cm in length and contained a minimum of 2 buds. Twenty cuttings were dipped in rooting hormone and placed in rooting media by the inventor at the home greenhouse at the above address. An additional 40 cuttings were delivered to Dr. Zachariah Miller at the nearby University research center. Rooting success for both batches exceeded 90%. The 'Harbinger' progeny were then planted both at the inventor's home (address above) and at the research center. From 2019 to 2024, the 'Harbinger' progeny have been evaluated and described by the inventor and Drs. Miller and Andrej Svyantek of the research center. Numerous botanical characteristics and physiological behaviors were recorded. During this time period, the 'Harbinger' progeny have behaved in every detail, similar to the original 'Harbinger' seedling. This indicates stability of the germplasm.

SUMMARY OF THE INVENTION

The distinguishing characteristics of 'Harbinger' grape are:

Physiology: The novel trait that gives 'Harbinger' its commercial appeal and separates it from all other wine grapes in its Market Class is the ability to ripen 3-4 weeks ahead of the existing cultivars. We have described ripening as having achieved a minimum of 25 Brix (% sugar) in the fruit. Table 1 below compares 'Harbinger' ripening with that of 'Marquette' (U.S. Plant Pat. No. 19579P3), the major red, cold-hardy, wine-grape grown in this region.

TABLE 1

Ripening Comparison of 'Harbinger' and 'Marquette (U.S. Plant Pat. No. 19579P3). The dates are when the grapes reached 25 Brix sugar content in Corvallis, MT.

| Year | 'Harbinger' | 'Marquette' |
|---|---|---|
| 2017 | 09/04 | 10/03 |
| 2018 | 09/09 | NR |
| 2019 | 09/05 | 10/06 |
| 2020 | 09/06 | 10/04 |
| 2021 | 09/10 | NR |
| 2022 | 09/08 | NR |
| 2023 | 09/03 | 09/29 |

NR=25 Brix not achieved before frost. 2017-2020=Original 'Harbinger Seedling, 2021-2023='Harbinger' Progeny.

BRIEF DESCRIPTION OF PHOTOGRAPHS

FIG. 1. The original 'Harbinger' seedling at 5 years of age, growing along a fence adjacent to a vineyard at 822 Promise Lane, Corvallis, MT. Photo was taken Sep. 5, 2019

Figure 2:
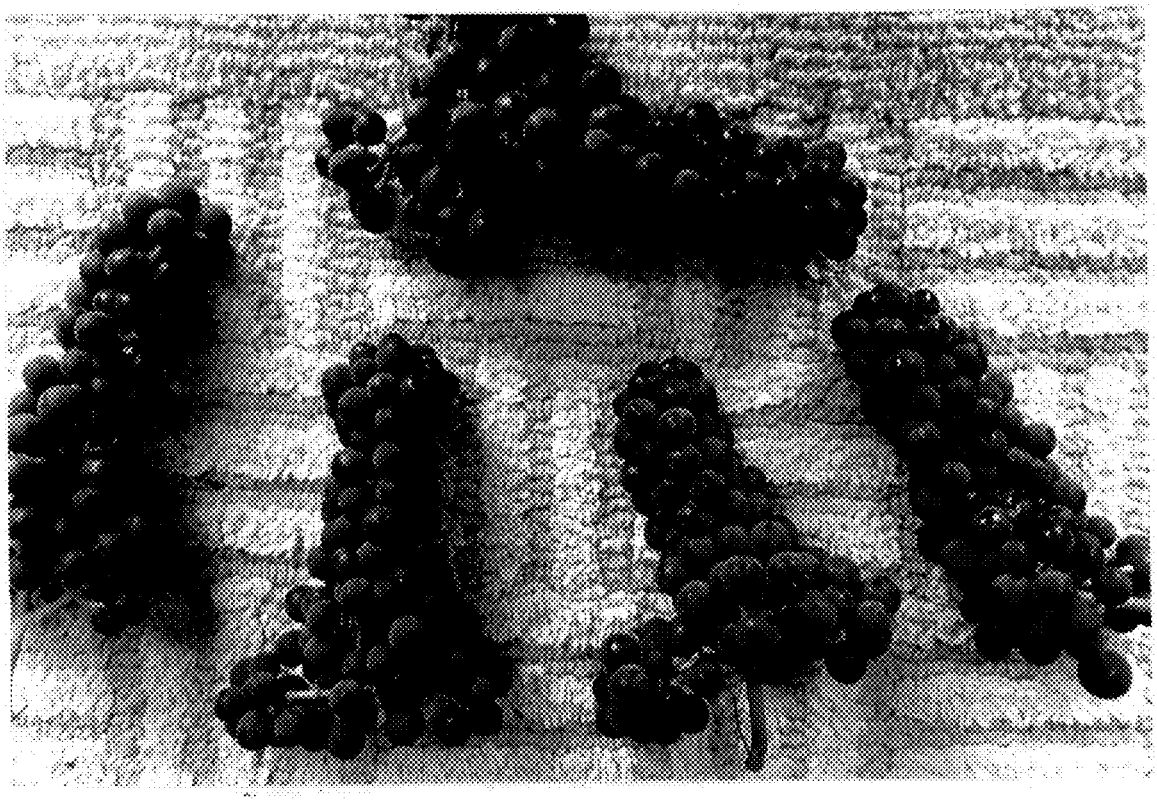
Figure 3A:
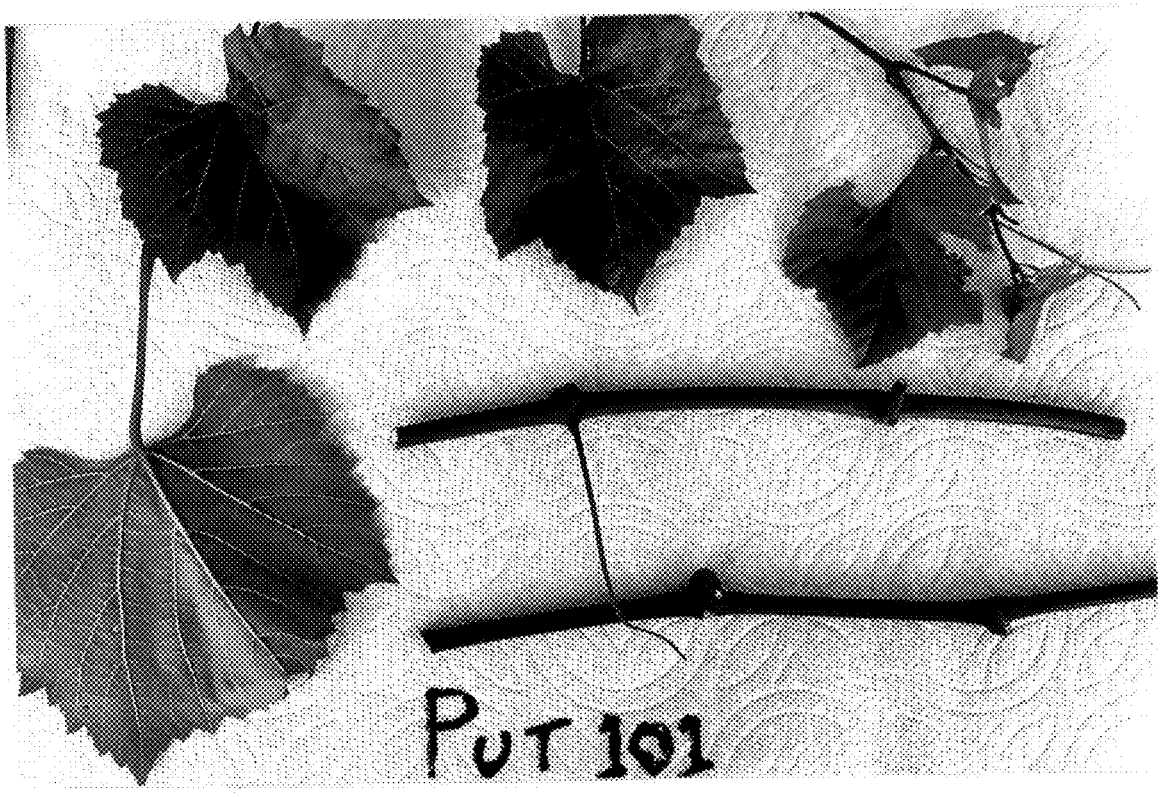

FIG. 2. Typical fruit clusters of 'Harbinger' harvested on Sep. 9, 2020. The berries measured 26 Brix sugar on this date FIG. 3*a*. New growth of 'Harbinger' shoots, showing young leaves, growing apex with tendrils, and red-pigmented stems FIG. 3*b*. Red stems and petioles, distinguishing features of 'Harbinger' grape FIG. 4. Mature leaves of 'Harbinger' grape with red pigmented petioles FIG. 5. Relative ripening in late August of 'Harbinger' and two red wine cultivars, 'Frontenac Gris' (U.S. Plant Pat. No. 16478P3) and 'Marquette' (U.S. Plant Pat. No. 19579P3) commonly grown in Western MT. PUT 102 was another seedling we were observing at the time.

Figure 6A:
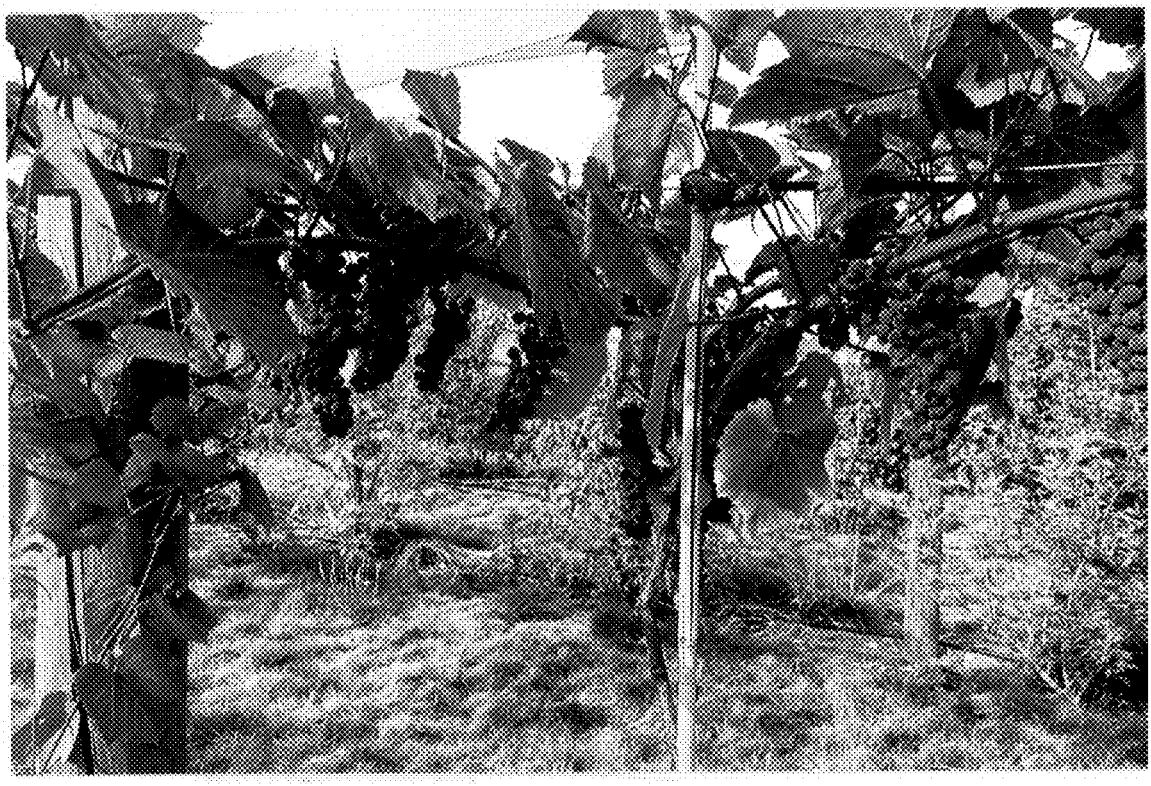
Figure 6B:
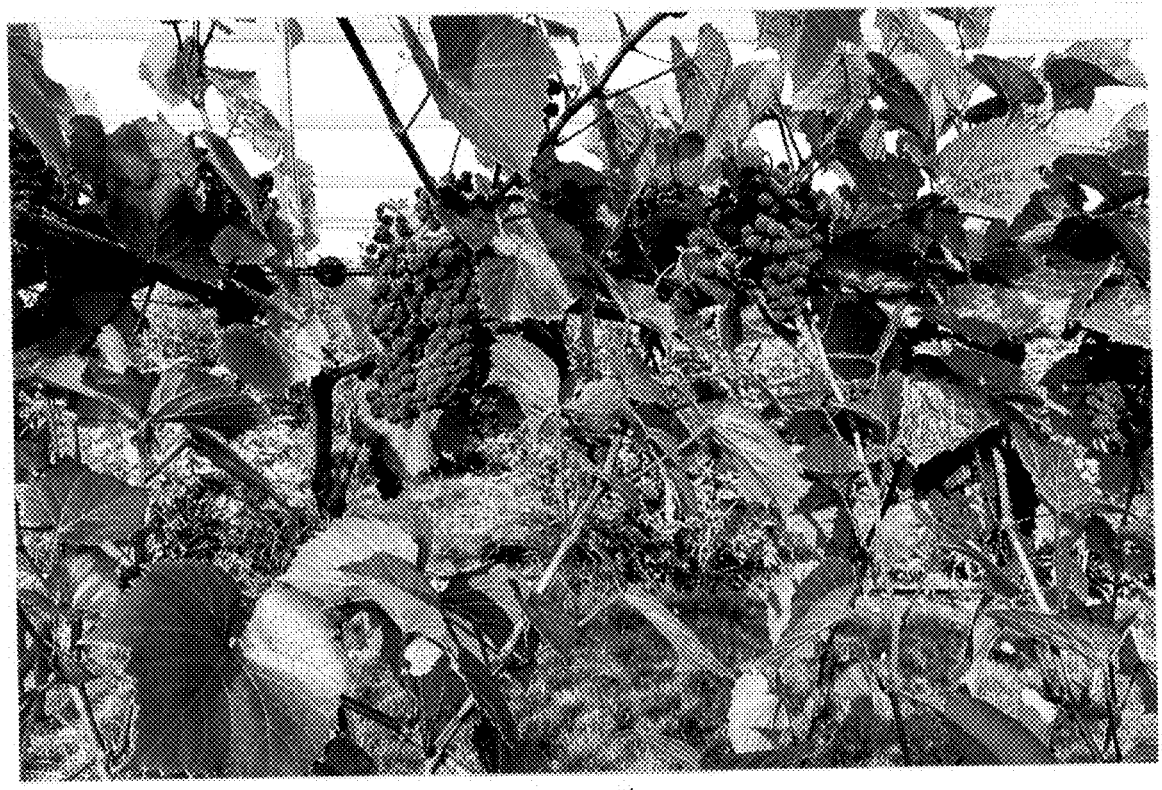

FIGS. 6*a* and 6*b*. Four year-old 'Harbinger' progeny growing at the Corvallis, MT Research Center on Sep. 7, 2023. Fruit measured 26 Brix sugar on that date

DETAILED BOTANICAL DESCRIPTION

Figure 3B:
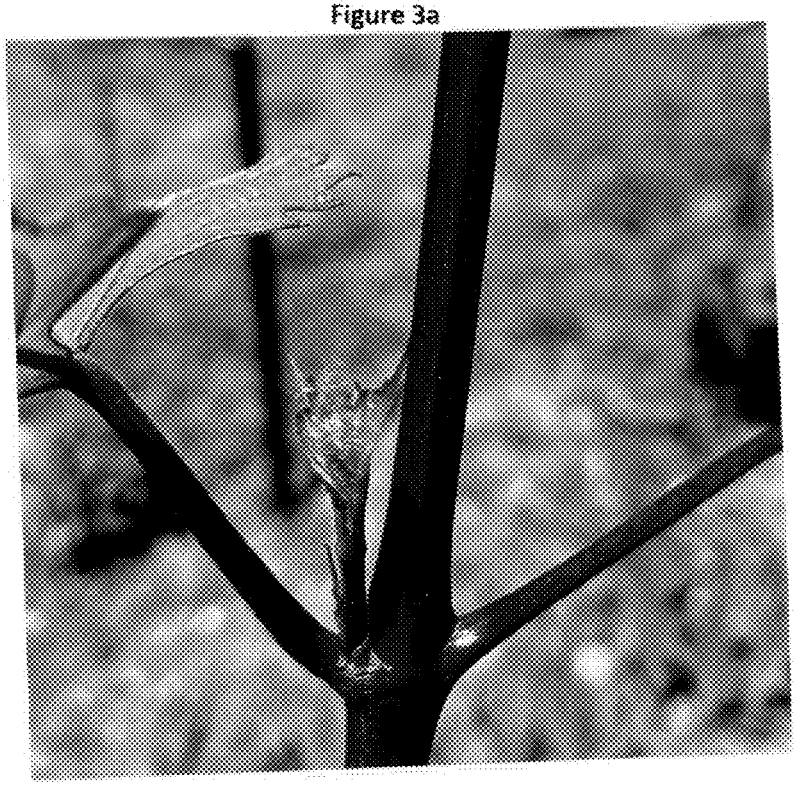
Figure 4:
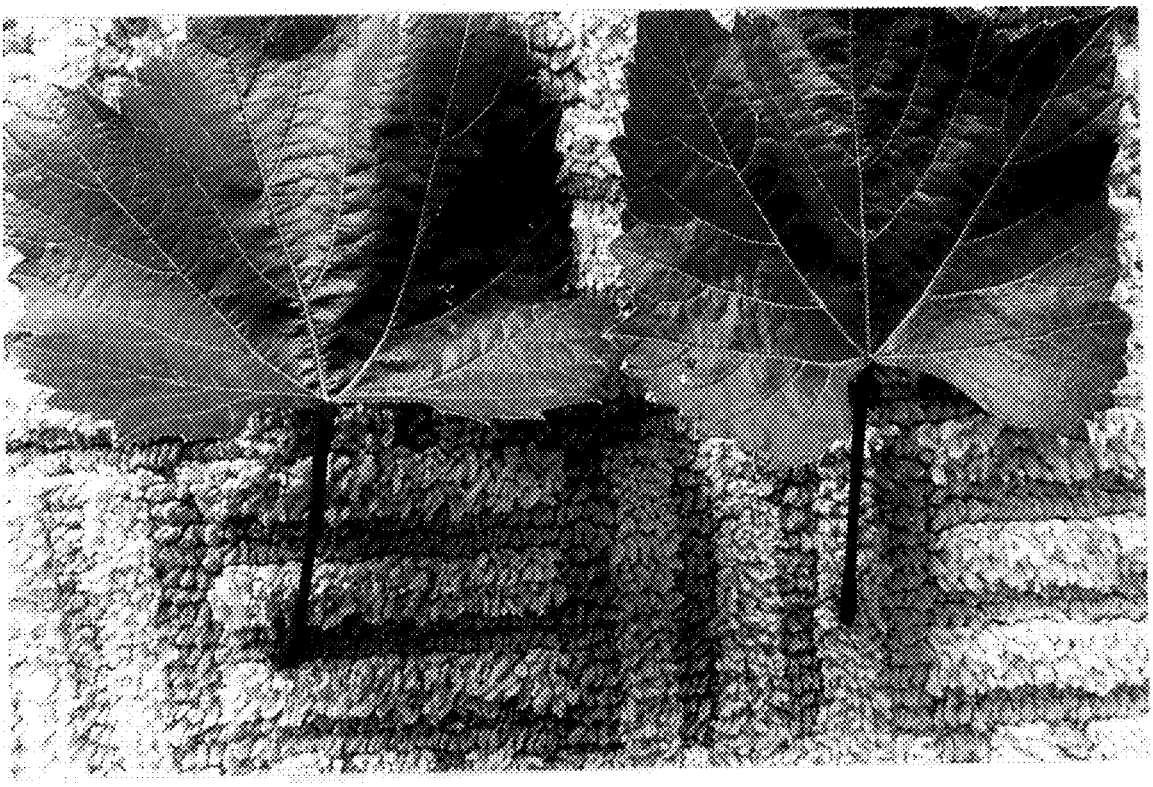
Figure 5:
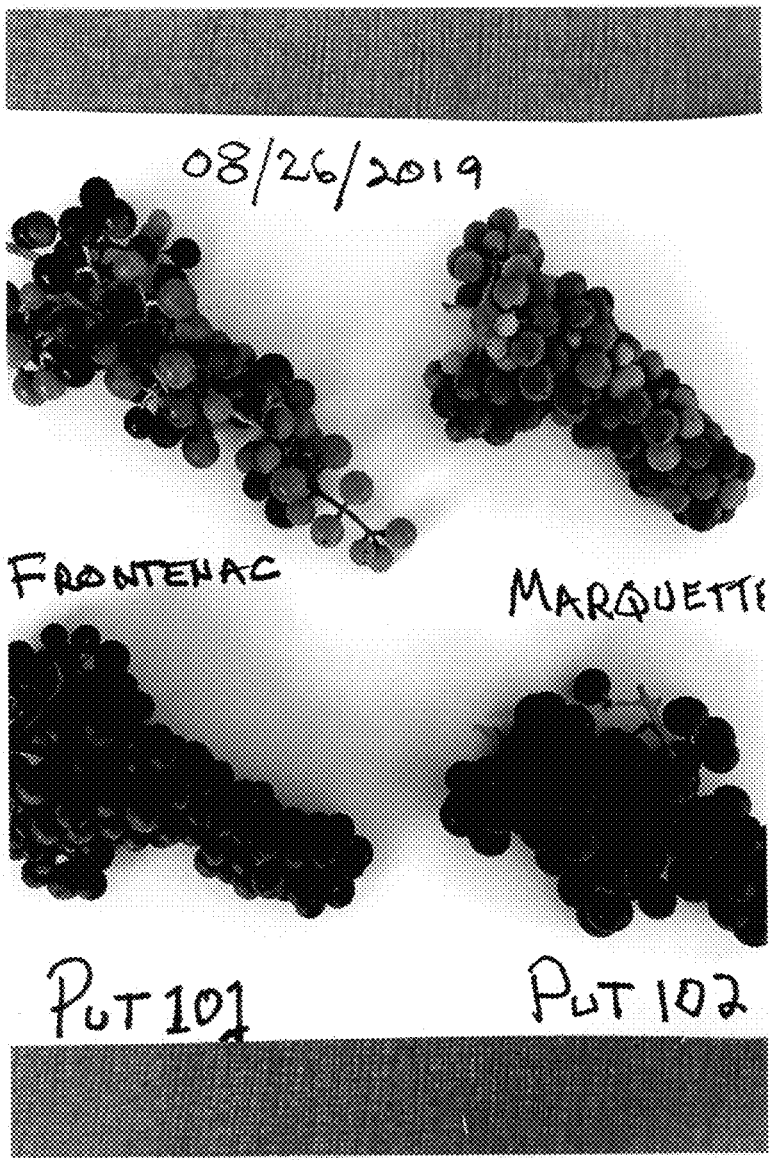

Botanical Characteristics: The feature of 'Harbinger' is a brilliant red pigmentation in the new growth, particularly in the stems, petioles and leaf veins (FIGS. 3-4). The inventor has observed well over a 100 grape cultivars in numerous countries over the past 60 years. This degree of pigmentation has not been observed before.

Bark: Texture is shredding and semi-flaking, color—197B-199A.

Berries: Medium size, 1.02 g +–0.10 g; Length=7.5-9.1 mm; Shape—elliptical to round; Skin color—103A with 98C bloom; Flesh=68C.

Buds: Triangular, 2.8-4.5 mm wide ×3.3-6.2 mm long, color is a blend of 166A and 178B.

Canes or stems: Annual shoot growth—0.87-1.75 m on 4 year-old vines on a high-wire cordon training system.; Growth of 1.47-2.33 m on 9 year-old original seedling Cane diameters—0.47-0.65 cm; Vigor is classified as medium.

Flowers: Blooms at similar dates as other cold-hardy red wine grapes (June 8-20); No remarkable features.

Fruit chemistry: On Sep. 9, 2022—Sugar=26 Brix, pH=3.04, Total acidity=11.04; On Sep. 12, 2023, Sugar=26.5 Brix, pH=3.18, Total acidity=10.5.

Fruit clusters: Medium size, 62.4 +–5.3 g, tight configuration (FIG. 2), often slightly T-shaped.

Leaf arrangement: Opposite (FIG. 3*b*).

Leaf characteristics: Palmate, 3-5 lobed, Dentate margins, Adaxial veins prominent, Length =10.6 +–1.2 cm, Width=11.7+–1.6 cm, Adaxial=144C, Abaxial=150B-149C; Sparse hairs.

Pedicils: 4.8mm.

Petioles: Length—8.8-11.4 cm; Distinct red pigmentation—187B.

Roots: No field excavations were made; Roots on newly propagated cuttings classified as vigorous, 12-17 roots/plant, Length=10.2-16.5 cm at 6 weeks. Grown on its own roots, no grafting done.

Seeds: Average size, 2.5 mm, Color blend of 199A, 187A and 183A.

Tendrils: Relatively strait and often forked, 3.3-6.5 cm, red pigmentation—187B, glabrous.

Trunks: Average diameters on 4 year-old vines=1.9 cm measured 5 cm above soil level. The 9 year-old original seedling measured 2.8 cm at 5 cm above soil level. Measurements taken Sep. 5, 2023. Trunk heights are determined by management choices.

Winter Hardiness: 'Harbinger' has shown good winter hardiness over a 9 year period. During that time, it has encountered numerous events of –16-18F. There has been no loss of vegetative growth or fruit yield due to winter damage. Its hardiness is comparable to other cultivars in its market class.

Yields: Based on projections from the original seedling and its progeny, a well-managed 'Harbinger' vineyard to yields about 3.5 tons of grapes per acre.

The invention claimed is:

1. A new and distinct grape plant named 'HARBINGER' as herein illustrated and described.

* * * * *